United States Patent
Iwasaki et al.

(10) Patent No.: US 10,172,764 B2
(45) Date of Patent: Jan. 8, 2019

(54) INFUSION BAG FILM AND INFUSION BAG USING INFUSION BAG FILM

(71) Applicant: HOSOKAWA YOKO CO., LTD., Tokyo (JP)

(72) Inventors: Toshiharu Iwasaki, Tokyo (JP); Saburou Unai, Tokyo (JP)

(73) Assignee: HOSOKAWA YOKO CO., LTD., Tokyo (JP)

(*) Notice: Subject to any disclaimer, the term of this patent is extended or adjusted under 35 U.S.C. 154(b) by 278 days.

(21) Appl. No.: 14/895,917

(22) PCT Filed: Jun. 5, 2014

(86) PCT No.: PCT/JP2014/064942
§ 371 (c)(1),
(2) Date: Dec. 3, 2015

(87) PCT Pub. No.: WO2014/196594
PCT Pub. Date: Dec. 11, 2014

(65) Prior Publication Data
US 2016/0120750 A1    May 5, 2016

(30) Foreign Application Priority Data
Jun. 7, 2013    (JP) .................................. 2013-121071

(51) Int. Cl.
*A61J 1/10*     (2006.01)
*B32B 27/32*    (2006.01)
(Continued)

(52) U.S. Cl.
CPC .............. *A61J 1/10* (2013.01); *A61L 31/041* (2013.01); *B32B 7/12* (2013.01); *B32B 27/08* (2013.01);
(Continued)

(58) Field of Classification Search
CPC .......... A61J 1/10; A61J 1/2024; A61J 1/2093; A61L 31/041; B32B 7/12; B32B 27/08;
(Continued)

(56) References Cited

U.S. PATENT DOCUMENTS

| 2008/0063825 A1* | 3/2008 | Mori | A61J 1/10 |
| | | | 428/36.6 |
| 2010/0080985 A1* | 4/2010 | Noda | B29C 55/12 |
| | | | 428/336 |

FOREIGN PATENT DOCUMENTS

| CN | 88103022 A | 11/1988 |
| CN | 1237192 A | 12/1999 |

(Continued)

OTHER PUBLICATIONS

Office Action dated Mar. 20, 2017 of Chinese Patent Application No. 201480032126.5.
(Continued)

*Primary Examiner* — Philip R Wiest
(74) *Attorney, Agent, or Firm* — Nixon Peabody LLP; Jeffrey L. Costellia (57) ABSTRACT

Disclosed is an infusion bag film including: a surface layer which is formed of a polyamide resin composition; a heat sealing layer which is formed of a polyethylene resin composition containing a polyethylene as a main component; and an adhesive layer which is provided between the surface layer and the heat sealing layer, in which the polyamide resin composition is obtained by blending 0.05 parts by mass to 1 part by mass of hydrotalcite with respect to 100 parts by mass of a polyamide resin formed of one or more of Nylon 11 and Nylon 12. An object of the invention is to provide an infusion bag film which has reduced eluate in a pH test, that is, has high hot water resistance even when a polyamide resin, which can be heat-sealed in a short period of time at a high temperature, but has a problem in the hot (Continued)

water resistance in some cases, is used in a surface layer, and an infusion bag using the infusion bag film.

5 Claims, 2 Drawing Sheets (51) Int. Cl.
B32B 27/08 (2006.01)
B32B 27/34 (2006.01)
A61L 31/04 (2006.01)
B32B 7/12 (2006.01)
B32B 27/18 (2006.01)
A61J 1/20 (2006.01)

(52) U.S. Cl.
CPC .............. *B32B 27/18* (2013.01); *B32B 27/32* (2013.01); *B32B 27/34* (2013.01); *A61J 1/2024* (2015.05); *A61J 1/2093* (2013.01); *B32B 2307/308* (2013.01); *B32B 2307/31* (2013.01); *B32B 2535/00* (2013.01)

(58) Field of Classification Search
CPC ......... B32B 27/18; B32B 27/32; B32B 27/34; B32B 7/01; B32B 7/34222
See application file for complete search history.

(56) References Cited

FOREIGN PATENT DOCUMENTS

| CN | 102574387 A | 7/2012 |
|---|---|---|
| CN | 102596144 A | 7/2012 |
| CN | 103068357 A | 4/2013 |
| EP | 1 803 778 A2 | 7/2007 |
| EP | 1 985 442 A1 | 10/2008 |
| EP | 2 258 549 A1 | 12/2010 |
| EP | 2 492 092 A1 | 8/2012 |
| JP | A-02-166159 | 6/1990 |
| JP | A-04-359064 | 12/1992 |
| JP | A-359064 | 12/1992 |
| JP | A-06-190990 | 7/1994 |
| JP | A-07-224204 | 8/1995 |
| JP | JA-A-07-224204 | 8/1995 |
| JP | 10-139941 A | 5/1998 |
| JP | 2002-121461 A | 4/2002 |
| JP | A-2010-201648 | 9/2010 |
| TW | 200927083 A | 7/2009 |
| TW | 200940046 A | 10/2009 |
| WO | WO 2006/043459 | 4/2006 |
| WO | WO 2008/075461 | 6/2008 |

OTHER PUBLICATIONS

Office Action dated Jun. 6, 2017 of Taiwanese Patent Application No. 103119746.

"Plastic Hygiene for Food", Ministry of Health and Welfare Environment and Health Administration Division of Food Chemistry, Kodansha Scientific Co. Ltd., Jul. 1, 1980.

The First Office Action, dated Jul. 6, 2016, issued in Chinese Patent Application No. 201480032126.5, 17 pages.

International Search Report issued in International Application No. PCT/JP2014/064942 dated Aug. 5, 2014, with English translation, 4 pages.

European Search Report dated Dec. 22, 2016 to EP Application No. 14807904.9, 5 pages.

\* cited by examiner

INFUSION BAG FILM AND INFUSION BAG USING INFUSION BAG FILM

CROSS-REFERENCE TO RELATED PATENT APPLICATION

The present application is a National Stage Application of International Application No. PCT/JP2014/064942 entitled "INFUSION BAG FILM AND INFUSION BAG USING INFUSION BAG FILM" filed Jun. 5, 2014, which claims priority to Japanese Patent Application Number 2013-121071 filed June 7, the contents of which are incorporated herein by reference in their entirety.

TECHNICAL FIELD

The present invention relates to an infusion bag film and an infusion bag using the infusion bag film.

BACKGROUND ART

As infusion bags which are used in infusion treatments in medical fields, blow-molded containers obtained by blow-molding a synthetic resin such as polyethylene, polypropylene, or polyvinyl chloride, or soft bags manufactured by heat-sealing a film are used. Among these, soft bags are widely used since these are light, have a small volume at the time of disposal, and do not require an air needle that causes nosocomial infection at the time of administration. In such soft bags, polyolefin films of polyethylene or polypropylene have been used which are eluted in small amounts when wet sterilization is performed thereon under high pressure and which have good transparency and flexibility.

However, when a polyolefin film is used, there is a problem in that the soft bag production efficiency per hour is low. That is, when a bag is manufactured by heat-sealing a polyolefin film in a short period of time at a high temperature in order to increase production efficiency, the surface damage of the film is severe and the film has an excessively reduced thickness due to the high-temperature and high-pressure conditions of the heat sealing. Thus, the bag is likely to easily break or may be broken. In order to avoid such a problem, the bag manufacturing process by heat sealing using a polyolefin film should be performed carefully for a long period of time.

A method using a lamination film in which a heat-resistant resin layer and a sealant layer formed of a resin which is melted at a lower temperature than a heat-resistant resin are laminated is examined in order to make it possible to perform heat sealing in a short period of time at a high temperature. For example, Patent Document 1 discloses a multi-layer film in which an outer layer formed of a heat-resistant polyamide resin layer, an adhesive resin layer, a flexible polyolefin-based resin intermediate layer, and a blocking-resistant polyolefin-based resin inner layer are laminated in order from the outside.

CITATION LIST

Patent Document

[Patent Document 1] Japanese Unexamined Patent Application, First Publication No. H6-190990

SUMMARY OF INVENTION

Technical Problem

However, the multi-layer film disclosed in Patent Document 1 has inadequate hot water resistance when the polyamide used in the heat-resistant polyamide resin layer is Nylon 6. Specifically, in an eluate test in The Japanese Pharmacopoeia, Sixteenth Edition, which is required to be performed on aqueous injection containers, a Nylon 6 film whitens or cracks when being heated in hot water at 121° C., and thus cannot meet standards. Such a problem in the hot water resistance is thought to be improved when using Nylon 11 or Nylon 12 in place of Nylon 6 as the polyamide. However, the applicant of the invention has found that in the case in which the thickness of the heat-resistant polyamide resin layer in the multi-layer film is increased and the amount of the polyamide used is increased, the amount of an eluate when the multi-layer film is held in hot water increases when using Nylon 11 or Nylon 12 as the polyamide. Specifically, when a pH test is performed in which a multi-layer film is held for a certain time in hot water at 121° C. to measure the pH of the hot water after the holding, the difference in the pH between the hot water and a blank test liquid increases. That is, elution of some kind of component which changes the pH in the hot water is shown and standards may not be met.

The invention is contrived in view of such circumstances, and an object thereof is to provide an infusion bag film which has reduced eluate in a pH test, that is, has excellent hot water resistance even when a polyamide resin, which can be heat-sealed in a short period of time at a high temperature but has a problem in the hot water resistance in some cases, is used in a surface layer, and an infusion bag using the infusion bag film.

Solution to Problem

The invention has the following configurations.

[1] An infusion bag film including: a surface layer which is formed of a polyamide resin composition; a heat sealing layer which is formed of a polyethylene resin composition containing a polyethylene as a main component; and an adhesive layer which is provided between the surface layer and the heat sealing layer, in which the polyamide resin composition is obtained by blending 0.05 parts by mass to 1 part by mass of hydrotalcite with respect to 100 parts by mass of a polyamide resin formed of one or more of Nylon 11 and Nylon 12.

[2] An infusion bag using the infusion bag film according to [1].

[3] The infusion bag according to [2] which is a multi-chamber infusion bag.

Advantageous Effects of Invention

According to the invention, it is possible to provide an infusion bag film which has reduced eluate in a pH test, that is, has excellent hot water resistance even when a polyamide resin, which can be heat-sealed in a short period of time at a high temperature but has a problem in the hot water resistance in some cases, is used in a surface layer, and an infusion bag using the infusion bag film.

DESCRIPTION OF EMBODIMENTS

Hereinafter, the invention will be described in detail.

Figure 1:
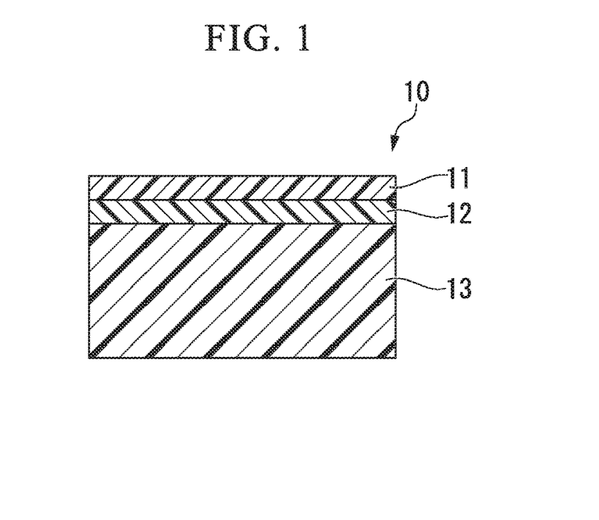
FIG. 1 is a longitudinal sectional view showing an example of an infusion bag film of the invention.
Figure 2A:
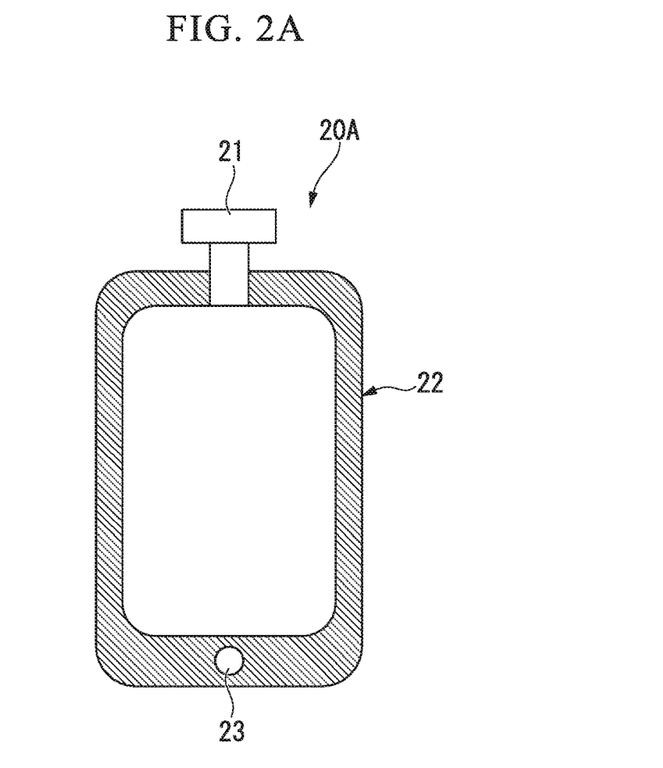
FIG. 2A is a plan view showing an example of an infusion bag using the infusion bag film of the invention.
Figure 2B:
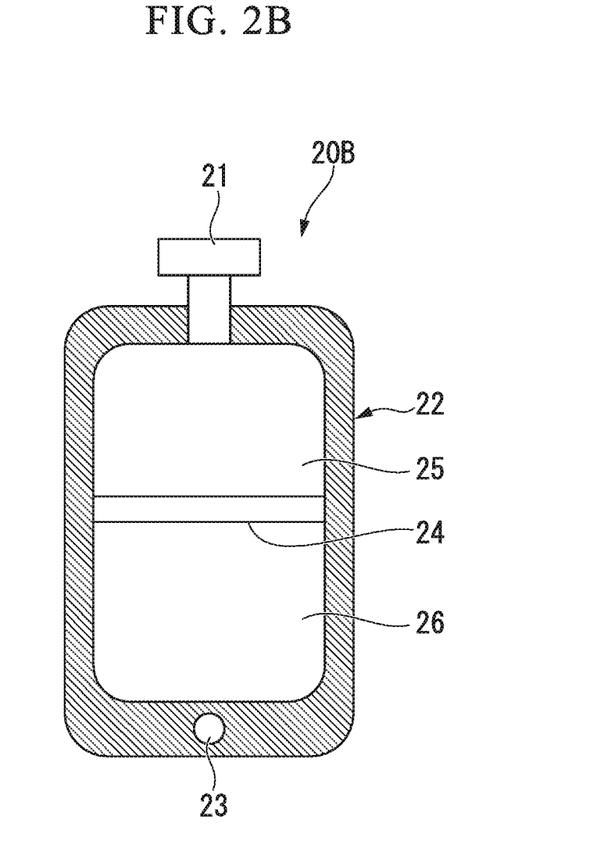
FIG. 2B is a plan view showing another example of the infusion bag using the infusion bag film of the invention.

FIG. 1 is a longitudinal sectional view showing a layer configuration of an example of an infusion bag film of the invention. FIGS. 2A and 2B are views showing the appearances of infusion bags using the infusion bag film of FIG. 1. FIG. 2A is a plan view of an infusion bag having one liquid housing chamber, and FIG. 2B is a plan view of a multi-chamber infusion bag having two liquid housing chambers.

An infusion bag film 10 in the example of FIG. 1 is a film having a three-layer-configuration in which a surface layer 11 and a heat sealing layer 13 are laminated with an adhesive layer 12 interposed therebetween.

The surface layer 11 is formed from a polyamide resin composition in which hydrotalcite is added to a polyamide resin formed of one or more of Nylon 11 and Nylon 12.

The surface layer 11 is a layer which becomes an outermost layer of an infusion bag 20A or 20B when the infusion bag 20A or 20B is manufactured using the infusion bag film 10 of FIG. 1. In addition, the surface layer 11 acts as a buffer layer which lessens film damage caused by the external heating performed on the infusion bag film 10 in the manufacturing of the infusion bag 20A or 20B to enable high-temperature and short-time heat sealing.

Specifically, in the manufacturing of the infusion bag 20A or 20B, a discharge and injection port member 21 such as a port or a tube for injecting or discharging an infusion is thermally welded to an infusion bag body 22 formed of the infusion bag film 10. In the case of the infusion bag film 10 in the example of FIG. 1, when such thermal welding is performed, the surface layer 11 acts as the above-described buffer layer by being positioned on the side of thermal welding means such as a hot plate for heat sealing in a heating state.

In FIGS. 2A and 2B, the shaded portions shown in peripheral portions of the infusion bags 20A and 20B are heat-sealed portions in which the heat sealing layers 13 are disposed opposed to each other and heat-sealed. The reference number 23 indicates a suspension hole for hanging the infusion bag 20A or 20B. FIG. 2B shows a multi-chamber infusion bag having two liquid housing chambers as described above, and the infusion bag 20B is partitioned into a first liquid housing chamber 25 and a second liquid housing chamber 26 by a weak sealing portion 24. The multi-chamber infusion bag is an infusion bag capable of storing infusions, of which the quality deteriorates when being stored for a long period of time in a mixed state, in separate liquid housing chambers until just before being administered to a patient. The weak sealing portion 24 is peeled when using the infusion bag 20B, and the liquid in the first liquid housing chamber 25 and the liquid in the second liquid housing chamber 26 are mixed together.

As the polyamide resin, at least one of Nylon 11 and Nylon 12 can be used. Nylon 11 is obtained by ring-opening and polycondensing undecane lactam. Nylon 12 is obtained by ring-opening and polycondensing lauryl lactam. Among these polyamide resins, Nylon 11 having a higher melting point of 184° C. to 188° C. than Nylon 12 having a melting point of 176° C. is preferably used. When using Nylon 11, the surface damage of the film when the infusion bag 20A or 20B is manufactured by heat-sealing the infusion bag film 10 can be further reduced and bag manufacturing at a higher speed is possible.

The hydrotalcite is a carbonate such as magnesium, calcium, zinc, aluminum, or bismuth, and is a hydrous basic carbonate containing crystalline water or a carbonate containing no crystalline water. The hydrotalcite includes natural products and synthetic products, and any of them can be used. In addition, these can be used regardless of the crystalline structure, crystal particle diameter, water content, and the like thereof. In general, the hydrotalcite is expressed by the following Expression (1).

$$Mg_{1-x}Al_x(OH)_2(CO_3)_{x/2} \cdot mH_2O \qquad (1)$$

(where x is more than 0 and is equal to or less than 0.5, and m is a number of 3 or less.)

Specific examples of the hydrotalcite include $Mg_4Al_2(OH)_{12}CO_3 \cdot 3H_2O$, $Mg_{4.3}Al_2(OH)_{12.6}CO_3 \cdot nH_2O$ (n is a number of 3 or less), $Mg_{4.5}Al_2(OH)_{13}CO_3 \cdot 3H_2O$, $Mg_{4.5}Al_2(OH)_{13}CO_3 \cdot 3.5H_2O$, and $Mg_5Al_2(OH)_{14}CO_3 \cdot 4H_2O$, $Mg_6Al_2(OH)_{16}CO_3 \cdot 4H_2O$.

The hydrotalcite is thought to act to suppress or absorb or to react with and neutralize a component eluted in hot water from the film 10 when the infusion bag film 10 is held in the hot water.

The amount of the hydrotalcite in the polyamide resin composition is 0.05 parts by mass to 1 part by mass, preferably 0.1 parts by mass to 0.8 parts by mass, and more preferably 0.15 parts by mass to 0.5 parts by mass with respect to 100 parts by mass of the polyamide resin. When the amount of the hydrotalcite is equal to or more than the lower limit value of the above range, the difference in the pH between hot water and a blank test liquid is sufficiently small in a pH test in which the infusion bag film 10 is held for 1 hour in the hot water at 121° C. to measure the pH of the hot water after the holding. That is, there is almost no eluate in the hot water, and as a result, standards can be met. When the amount of the hydrotalcite is more than the upper limit value of the above range, the remaining residue on ignition increases and standards cannot be met when the infusion bag film 10 is heated under predetermined conditions, that is, under conditions prescribed as a residue on ignition test method in the general test methods of The Japanese Pharmacopoeia, Sixteenth Edition.

The pH test is a plastic aqueous injection container test method, is an eluate test, and is a test in which determination is performed with pH, prescribed in The Japanese Pharmacopoeia, Sixteenth Edition. An outline thereof is as follows.

A cut film piece having a certain area and water are put into a glass container, heated for a predetermined length of time at a predetermined temperature using a high-pressure steam sterilizer, and then left until the temperature is lowered to room temperature. A test liquid which is the content liquid at that time and a blank test liquid in which no cut film piece is added are subjected to a predetermined process, and then the pH of both of the liquids is measured and the difference therebetween is calculated. When the difference is large, the amount of change in the pH of the infusion in the infusion bag is large when high-pressure steam sterilization is performed to secure hygiene of the infusion, liquid properties of the infusion change, and the quality of the infusion is affected.

In addition, the residue on ignition test is a test which is used to know the content of inorganic matter contained as impurities in organic matter, and a standard value is prescribed in standards of plastic aqueous injection containers and polyethylene or polypropylene aqueous injection containers in The Japanese Pharmacopoeia, Sixteenth Edition. When the content of the inorganic matter as impurities does not meet standards, the container cannot be used as an aqueous injection container.

The thickness of the surface layer 11 is preferably 2% to 15%, more preferably 2% to 10%, and particularly preferably 2% to 8% when a total thickness of the infusion bag film 10 is 100%.

When the thickness of the surface layer 11 is equal to or more than the lower limit value of the above range, the film damage caused by the heat transfer in the heat sealing can be sufficiently buffered. When the thickness of the surface layer 11 is equal to or less than the upper limit value of the above range, the stiffness of the infusion bag film 10 does not significantly increase, and thus the infusion bag 20A or 20B manufactured using the film 10 has good flexibility. In the above-described pH test, when the thickness of the surface layer 11 is equal to or less than the upper limit value of the above range, the difference in the pH between the test liquid and the blank test liquid is sufficiently small, and standards are easily met.

The heat sealing layer 13 is a layer which is melted and bonded by heat when molding the infusion bag film 10 into a bag shape. The heat sealing layer 13 is formed of a polyethylene resin composition containing a polyethylene as a main component.

In this specification, the main component is a component contained in an amount more than 50 mass % in 100 mass %.

The polyethylene resin composition used in the heat sealing layer 13 of this embodiment contains 50 mass % or more, preferably 60 mass % or more, and more preferably 70 mass % or more of a polyethylene. The heat sealing layer 13 is particularly preferably formed only of a polyethylene having excellent hygiene since it configures a heat sealing surface and is also a layer which forms a surface coming into contact with the content.

Examples of the polyethylene include low-density polyethylenes (LD), high-density polyethylenes (HD), linear low-density polyethylenes (LLD), and one or more kinds of these can be used. The heat sealing layer 13 may consist of a single layer or multiple layers. For example, the heat sealing layer can consist of a single layer, and for this layer, one or two or more kinds selected from low-density polyethylenes, high-density polyethylenes, and linear low-density polyethylenes can be used. In addition, the heat sealing layer 13 can consist of two or more layers, and for the respective layers, one or two or more kinds selected from low-density polyethylenes, high-density polyethylenes, and linear low-density polyethylenes can be used. Examples of the heat sealing layer 13 consisting of two layers include a two-layered heat sealing layer consisting of a layer formed of a linear low-density polyethylene and a layer formed of a high-density polyethylene in which the layer formed of a high-density polyethylene is a layer configuring a heat sealing surface; a heat sealing layer in which two layers which are different in mixing ratio between a linear low-density polyethylene and a high-density polyethylene are combined; and a two-layered heat sealing layer consisting of a layer formed of a mixture of a linear low-density polyethylene and a high-density polyethylene and a layer formed of a high-density polyethylene in which the layer formed of a high-density polyethylene is a layer configuring a heat sealing surface. Particularly, an infusion bag film in which a layer formed of a high-density polyethylene in a heat sealing layer is a layer configuring a heat sealing surface is preferred since the infusion bag film has excellent flexibility and anti-blocking properties so that the heat sealing surfaces are not mutually blocked. In addition, a case in which a layer formed of a high-density polyethylene in a heat sealing layer is a layer configuring a heat sealing surface, and a layer adjacent to an adhesive layer is a layer formed of a mixture of a linear low-density polyethylene and a high-density polyethylene is preferred since more excellent heat resistance and film appearance are provided than in a case in which the layer adjacent to the adhesive layer is a layer formed of a linear low-density polyethylene.

In this specification, the low-density polyethylenes are also called high-pressure low-density polyethylenes, and have a density of 910 kg/m$^3$ to 930 kg/m$^3$. Among these, low-density polyethylenes having a melt mass flow rate (hereinafter, referred to as "MFR") of 0.1 g/10 min to 20 g/10 min are preferred.

In this specification, the high-density polyethylenes are polyethylenes having a density of 940 kg/m$^3$ to 970 kg/m$^3$. Among these, high-density polyethylenes having a MFR of 0.1 g/10 min to 20 g/10 min are preferred.

In this specification, the linear low-density polyethylenes are copolymers of an ethylene and one or more α-olefins selected from α-olefins having 3 to 20 carbon atoms.

The α-olefins having 3 to 20 carbon atoms are preferably α-olefins having 3 to 12 carbon atoms. Specific examples thereof include propylene, 1-butene, 1-pentene, 4-methyl 1-pentene, 1-hexene, 1-octene, 1-decene, and 1-dodecene. Propylene, 1-butene, 1-hexene, and 1-octene are preferred.

The content of the α-olefin occupying the copolymer is usually 1 mol % to 30 mol %, and preferably 3 mol % to 20 mol %.

The density of the linear low-density polyethylenes is 900 kg/m$^3$ to 940 kg/m$^3$, and among these, linear low-density polyethylenes having a MFR of 0.1 g/10 min to 20 g/10 min are preferred.

In this specification, the density of each polyethylene is measured using a JIS K 7112 D method. The MFR is a value measured based on JIS K 7210 under conditions of a temperature of 190° C. and a load of 21.18 N.

The thickness of the heat sealing layer 13 is preferably 70% to 96%, more preferably 73% to 95%, and particularly preferably 75% to 90% when the total thickness of the infusion bag film 10 is set to 100%. When the thickness of the heat sealing layer 13 is equal to or more than the lower limit value of the above range, the film has sufficient strength properties. When the thickness of the heat sealing layer 13 is equal to or less than the upper limit value of the above range, the thicknesses of the surface layer 11 and the adhesive layer 12 are relatively sufficient.

The adhesive layer 12 is an interlayer adhesive layer between the surface layer 11 and the heat sealing layer 13 in the infusion bag film 10 having a three-layer-configuration. The adhesive layer 12 is preferably a layer formed of an adhesive resin containing, as a main component, a copolymer of an olefin polymer composed of an ethylene, a propylene, or a combination thereof and an unsaturated monomer such as an unsaturated carboxylic acid monomer or an anhydride monomer of an unsaturated dicarboxylic acid. Specifically, a graft copolymer in which an unsaturated monomer is graft-copolymerized with the above-described olefin polymer is suitable for the adhesive layer 12.

The unsaturated monomer to be graft-copolymerized is a compound having at least one double bond and containing at least one carboxyl group or an anhydride (group) thereof. Specific examples thereof include (meth)acrylic acid, maleic acid, itaconic acid, citraconic acid, endic acid, maleic anhydride, itaconic anhydride, endic anhydride, and citraconic anhydride, and one or more can be used.

The amount of the unsaturated monomer used when manufacturing a graft copolymer is 0.01 parts by mass to 20 parts by mass, and preferably 0.05 parts by mass to 10 parts by mass with respect to 100 parts by mass of the above-described olefin polymer. When the content of the unsaturated monomer is equal to or more than the lower limit value of the above range, sufficient adhesiveness is exhibited. When the content of the unsaturated monomer is equal to or less than the upper limit value of the above range, the amount of the unreacted unsaturated monomer in the manufacturing of the graft copolymer is reduced, and thus sufficient adhesiveness is exhibited.

As the adhesive resin formed of the graft copolymer used in the adhesive layer 12, commercially available products such as "Modic" and "Zelas" manufactured by Mitsubishi Chemical Corporation, "Adtex" manufactured by Japan Polyethylene Corporation, and "Admer" manufactured by Mitsui Chemicals, Inc. may be used.

The thickness of the adhesive layer 12 is preferably 1% to 30%, more preferably 1% to 20%, and particularly preferably 1% to 10% when the total thickness of the infusion bag film 10 is set to 100%. When the thickness of the adhesive layer 12 is within the above range, the surface layer 11 and the heat sealing layer 13 can be allowed to sufficiently adhere to each other, and an excessive increase in the total thickness of the infusion bag film is suppressed.

The surface layer 11 and the adhesive layer 12 of the infusion bag film 10 may contain a polyethylene, a polypropylene and other synthetic resins without departing from the gist of the invention. When the surface layer 11 and the adhesive layer 12 of the infusion bag film 10 contain a polyethylene, a polypropylene and other synthetic resins, these are preferably contained in an amount of 40 mass % or less, and more preferably 30 mass % or less in 100 mass % of the material (composition) of each layer.

The heat sealing layer 13 is formed from a polyethylene resin composition containing a polyethylene as a main component. The polyethylene resin composition may contain a polypropylene and other synthetic resins. When the polyethylene resin composition contains a polypropylene and other synthetic resins, these are preferably contained in an amount of 50 mass % or less, and more preferably 30 mass % or less in the polyethylene resin composition.

The infusion bag film 10 illustrated in FIG. 1 has a three-layer-configuration, but may have one or more layers other than the surface layer 11, the adhesive layer 12, and the heat sealing layer 13. In that case, two or more adhesive layers may be provided. Examples of other layers include an ethylene-vinyl alcohol copolymer, a resin layer formed of one or more selected from resins such as a cyclic polyolefin resin, a polyolefin resin, and a polyester resin, and metallic foil such as aluminum foil. Examples of the polyester resin include a polyethylene terephthalate resin and a polybutylene terephthalate resin. Specific examples of the layer configuration include layer configurations in which respective layers are provided in order, such as a layer configuration having a surface layer, an adhesive layer, a polyethylene terephthalate resin layer, an adhesive layer, and a heat sealing layer, a layer configuration having a surface layer, an adhesive layer, an ethylene-vinyl alcohol copolymer, an adhesive layer, and a heat sealing layer, and a layer configuration having a surface layer, an adhesive layer, aluminum foil, an adhesive layer, and a heat sealing layer.

The total thickness of the infusion bag film 10 is 50 μm to 1000 μm, and preferably 70 μm to 600 μm.

The surface layer 11, the heat sealing layer 13, and the adhesive layer 12 may have such a thickness that the ratio of the thickness of each layer occupying the total thickness of the infusion bag film 10 is within the above-described range. For example, the thickness of the surface layer 11 formed of a polyamide resin composition is preferably 35 μm or less, more preferably 25 μm or less, and particularly preferably 18 μm or less. In addition, the thickness of the surface layer 11 formed of a polyamide resin composition is preferably 8 μm or more. When the surface layer 11 formed of a polyamide resin composition has a thickness that is too large, the numerical value in the above-described pH test may increase.

The thickness of the heat sealing layer 13 is, for example, 30 μm to 270 μm, and the thickness of the adhesive layer 12 is, for example, approximately 5 μm to 50 μm.

The infusion bag film 10 can be obtained by, for example, multi-layer T-die molding, multi-layer coextrusion inflation molding, or the like. When multi-layer coextrusion inflation molding is employed, a film having excellent transparency can be obtained, and thus a water cooling inflation method is preferably employed.

Using such an infusion bag film 10, the infusion bag body 22 is manufactured by allowing the heat sealing layers 13 to be opposed to each other and by heat-sealing peripheral portions so as not to be peeled from each other, and the discharge and injection port member 21 is attached thereto by thermal welding to be able to manufacture, for example, the infusion bag 20A or 20B as shown in FIGS. 2A and 2B. When manufacturing the infusion bag 20B of FIG. 2B, the peelable weak sealing portion 24 is formed.

Such infusion bags 20A and 20B are manufactured using the infusion bag film 10 which has the surface layer 11 formed of a polyamide resin composition capable of being heat-sealed in a short period of time at a high temperature, and has reduced eluate in a pH test. Therefore, excellent production efficiency can be achieved, liquid properties of an infusion to be housed can be maintained, and the high quality of the infusion can be maintained.

EXAMPLES

Hereinafter, the invention will be described in detail with examples.

Example 1

Using materials shown in Table 1, an infusion bag film having a width of 200 mm and a total thickness of 250 μm in which a surface layer, an adhesive layer, and a heat sealing layer were provided in order was obtained by molding with a water cooling inflation film molding machine. That is, a polyamide resin composition in which 0.5 parts by mass of hydrotalcite was added to 100 parts by mass of Nylon 11 (PA11) was used in the surface layer, a maleic anhydride grafted polypropylene resin (AD) was used in the adhesive layer, and a mixed resin including 60 mass % of a linear low-density polyethylene (LLD), 20 mass % of a high-density polyethylene (HD), and 20 mass % of a high-pressure low-density polyethylene (LD) was used in the heat sealing layer.

The set temperature in the molding was 250° C. The surface layer had a thickness of 15 the adhesive layer had a thickness of 15 and the heat sealing layer had a thickness of 220 μm.

Whether the obtained infusion bag film met the following standards ((1) and (2) in the following "Evaluation") of polyethylene or polypropylene aqueous injection containers, plastic medicine container test methods, general test methods, the first section of The Japanese Pharmacopoeia, Sixteenth Edition was judged. In addition, the film appearance ((3) in the following "Evaluation") was also evaluated. The evaluation results are shown in Table 1.

subjected to steam sterilization under conditions of 30 minutes at 121° C., the presence or absence of whitening

TABLE 1

| | Surface Layer (15 μm) | | | Heat Sealing Layer (220 μm) | | Evaluation | | |
|---|---|---|---|---|---|---|---|---|
| | Polyamide Resin Kind | Amount of Hydrotalcite Added with respect to 100 Parts by Mass of Polyamide Resin (parts by mass) | Adhesive Layer (15 μm) Resin Kind | Layer Adjacent to Adhesive Layer (205 μm) | Layer Which is Not Adjacent to Adhesive Layer and Configures Heat Sealing Surface (15 μm) | Japanese Pharmacopeia Test Difference in pH in pH Test | Residue on Ignition (%) | Film Appearance Presence or Absence of Whitening |
| Example 1 | PA11 | 0.5 | AD | LLD (60 mass %) HD (20 mass %) LD (20 mass %) | | 0.8 | 0.04 | None |
| Example 2 | PA11 | 0.07 | AD | LLD (80 mass %) HD (20 mass %) | HD | 1.2 | 0.01 | None |
| Example 3 | PA11 | 0.9 | AD | LLD (80 mass %) HD (20 mass %) | HD | 0.5 | 0.08 | None |
| Comparative Example 1 | PA6 | 0.5 | AD | LLD (80 mass %) HD (20 mass %) | HD | — | — | Whitening |
| Comparative Example 2 | PA11 | 0.03 | AD | LLD (80 mass %) HD (20 mass %) | HD | 1.6 | 0.01 | None |
| Comparative Example 3 | PA11 | 1.2 | AD | LLD (80 mass %) HD (20 mass %) | HD | 0.3 | 0.11 | None |

The used resins and hydrotalcite are as follows.

PA6: Nylon 6, manufactured by Ube Industries, Ltd., UBE Nylon "1024B", density=1.14 g/cm$^3$, melt peak temperature=223° C.

PA11: Nylon 11, manufactured by Arkema K.K., RIL-SAN "BESV 0 A FDA", density=1.02 g/cm$^3$, melt peak temperature=184° C. to 188° C.

PA12: Nylon 12, manufactured by Arkema K.K., RIL-SAN "AESN 0 TL", density=1.01 g/cm$^3$, melt peak temperature=176° C.

AD: maleic anhydride grafted polypropylene, ZELAS "MC721AP" manufactured by Mitsubishi Chemical Corporation, density=0.89 g/cm$^3$, MFR=3.5 g/10 min, melt peak temperature=155° C.

LLD: linear low-density polyethylene, manufactured by Prime Polymer Co., Ltd., Evolue "SP0511", density=903 kg/m$^3$, MFR=1.2 g/10 min, melt peak temperature=110° C.

HD: high-density polyethylene, manufactured by Japan Polyethylene Corporation, Novatec, density=955 kg/m$^3$, MFR=3.5 g/10 min, melt peak temperature=132° C.

Hydrotalcite: $Mg_{4.5}Al_2(OH)_{13}CO_3 \cdot 3.5H_2O$, manufactured by Kyowa Chemical Industry Co., Ltd., DHT-4A LD: high-pressure low-density polyethylene, manufactured by Japan Polyethylene Corporation, density=927 kg/m$^3$, MFR=0.8 g/10 min, melt peak temperature=117° C.

"Evaluation" (1) pH Test: An eluate test was performed for 1 hour at 121° C. using a film cut into a strip shape to measure the pH. In order to meet standards, the difference in the pH between a test liquid and a blank test liquid is required to be 1.5 or less.

(2) Residue on Ignition: 5 g of the film was precisely weighed and residue on ignition measurement was performed. In order to meet standards, the residue on ignition is required to be 0.1% or less.

(3) Film Appearance: Two films were used, and heat sealing layers were overlapped to be opposed to each other and were heat-sealed to manufacture a bag of 20 cm×20 cm. The bag was filled with 300 mL of water to obtain a pouch, and with respect to the film appearance after the pouch was subjected to steam sterilization under conditions of 30 minutes at 121° C., the presence or absence of whitening was evaluated. In addition, when there was a portion in which inner surfaces of the pouch tightly adhered to each other after the steam sterilization, the surfaces were peeled from each other to visually evaluate the degree of the whitening of the peeling surface.

Examples 2 and 3, Comparative Examples 1 to 3

Infusion bag films having a width of 200 mm and a total thickness of 250 μm were obtained by molding with a water cooling inflation film molding machine in the same manner as in Example 1, except that surface layers, adhesive layers, and heat sealing layers shown in Table 1 were provided in order. However, the heat sealing layer had a two-layer-configuration, and among the heat sealing layers, the layer adjacent to the adhesive layer was set to have a thickness of 205 μm, and the layer which was not adjacent to the adhesive layer and configured a heat sealing surface was set to have a thickness of 15 μm. The obtained films were evaluated in the same manner as in Example 1. The evaluation results are shown in Table 1.

In Comparative Example 1, since whitening was recognized in the film appearance, the pH test and the residue on ignition test were not performed.

As shown in Table 1, the infusion bag films having a surface layer formed from a resin composition using PA11 as a polyamide resin and containing an appropriate amount of hydrotalcite had reduced eluate in a pH test, had less residue on ignition, and were not recognized as exhibiting film whitening caused by steam sterilization.

Examples 4 and 5

In Example 4, Nylon 11 (PA11) was used as a polyamide resin, and in Example 5, Nylon 12 (PA12) was used as a polyamide resin to form a surface layer using a polyamide resin composition in which 0.25 parts by mass was added to 100 parts by mass of the polyamide resin. Except for these points, infusion bag films were molded and evaluated in the same manner as in Example 2. The evaluation results are shown in Table 2.

For the purpose of checking the degree of the damage to the infusion bag film in the heat sealing, the heat sealing was performed at different heat sealing temperatures for different lengths of heat sealing time to evaluate the degree of the damage at that time through visual observation and peeling strength measurement. The evaluation was performed with the following 8-stage evaluation criteria.

D+: There is no damage of the outer surface of the film, but no sealing is provided.

D−: The thickness of the outer surface of the film is significantly reduced, and the peeling strength is strong. The peeling strength is 50 N/15 mm or more.

D−−: The thickness of the outer surface of the film is significantly reduced, the melted film partially adheres to holes and the sealing plate, and the peeling strength is strong. The peeling strength is 50 N/15 mm or more.

TABLE 2

| | Surface Layer (15 μm) | | | Heat Sealing Layer (220 μm) | | Evaluation | | | |
|---|---|---|---|---|---|---|---|---|---|
| | Polyamide Resin Kind | Amount of Hydrotalcite Added with respect to 100 Parts by Mass of Polyamide Resin (parts by mass) | Adhesive Layer (15 μm) Resin Kind | Layer Adjacent to Adhesive Layer (205 μm) | Layer Which is Not Adjacent to Adhesive Layer and Configures Heat Sealing Surface (15 μm) | Japanese Pharmacopeia Test Difference in pH in pH Test | Residue on Ignition (%) | Film Appearance Presence or Absence of Whitening | Peeling Surface Presence or Absence of Whitening |
| Example 4 | PA11 | 0.25 | AD | LLD (80 mass %) HD (20 mass %) | HD | 0.7 | 0.03 | None | None |
| Example 5 | PA12 | 0.25 | AD | LLD (80 mass %) HD (20 mass %) | HD | 0.6 | 0.04 | None | None |
| Example 6 | PA11 | 0.25 | AD | LLD (100 mass %) | HD | 0.7 | 0.03 | None*) | None |
| Example 7 | PA11 | 0.25 | AD | LLD (80 mass %) HD (20 mass %) | LLD (20 mass %) HD (80 mass %) | 0.7 | 0.03 | None | Whitening |

*)Whitening is not exhibited, but fine wrinkles are shown.

Specifically, two infusion bag films were prepared, and heat sealing layers were overlapped to be opposed to each other to perform heat sealing using a pair of upper and lower heat sealing plates having a temperature raised to a predetermined temperature (heat sealing temperature). Four heat sealing temperatures were set: 180° C., 200° C., 220° C., and 240° C. The heat sealing pressure was set to 0.2 MPa. Four heat sealing times were set: 0.1 seconds, 0.3 seconds, 0.5 seconds, and 1.0 second. However, two heat sealing times were selected from the four heat sealing times in accordance with heat sealing properties of each infusion bag film.

The sample heat-sealed in this manner was visually observed.

The sample was cut into a strip shape having a width of 15 mm and subjected to 180-degree peeling at a tensile rate of 300 mm/min using a tensile testing machine based on JIS-K6854-3.

The results are shown in Table 3.

(Evaluation Criteria)

A: There is no damage of the outer surface of the film, and the peeling strength is also strong. The peeling strength is 50 N/15 mm or more.

B+: There is no damage of the outer surface of the film, but the peeling strength is slightly weak. The peeling strength is 30 N/15 mm to 50 N/15 mm.

B−: A slight reduction in the thickness due to the damage of the outer surface of the film is shown, but the peeling strength is strong. The peeling strength is 50 N/15 mm or more.

C+: There is no damage of the outer surface of the film, but the peeling strength is weak. The peeling strength is less than 30 N/15 mm.

C−: A reduction in the thickness due to the damage of the outer surface of the film is shown, and the peeling strength is strong. The peeling strength is 50 N/15 mm or more.

TABLE 3

| | Heat Sealing Temperature (° C.) | Heat Sealing Time (seconds) | Evaluation Result |
|---|---|---|---|
| Example 4 | 180 | 0.5 | D+ |
| | | 1.0 | B+ |
| | 200 | 0.5 | A |
| | | 1.0 | A |
| | 220 | 0.3 | A |
| | | 0.5 | A |
| | 240 | 0.3 | A |
| | | 0.5 | A |
| Example 5 | 180 | 0.5 | C+ |
| | | 1.0 | A |
| | 200 | 0.5 | A |
| | | 1.0 | A |
| | 220 | 0.3 | A |
| | | 0.5 | A |
| | 240 | 0.3 | C− |
| | | 0.5 | D− |
| Example 6 | 180 | 0.5 | D+ |
| | | 1.0 | B+ |
| | 200 | 0.5 | A |
| | | 1.0 | A |
| | 220 | 0.3 | A |
| | | 0.5 | A |
| | 240 | 0.3 | A |
| | | 0.5 | A |
| Example 7 | 180 | 0.5 | B+ |
| | | 1.0 | A |
| | 200 | 0.5 | A |
| | | 1.0 | A |
| | 220 | 0.3 | A |
| | | 0.5 | A |
| | 240 | 0.3 | A |
| | | 0.5 | A |

As shown in Tables 2 and 3, also in Example 5 using Nylon 12 (PA12) as the polyamide resin of the surface layer, the eluate in a pH test was reduced, less residue on ignition was produced, and film whitening caused by steam sterilization was recognized as in Example 4 using Nylon 11 (PA11).

In addition, in any of Examples 4 and 5, with heat sealing in a short period of time of 0.3 seconds to 1.0 second at a high temperature of 200° C. to 220° C., it was possible to perform sealing with sufficient peeling strength without causing damage to the outer surface of the film. Particularly, in Example 4 using Nylon 11 (PA11) as a polyamide resin of the surface layer, the sealing was possible without problems even at a high temperature of 240° C.

Example 6 in which the layer adjacent to an adhesive layer is formed of a linear low-density polyethylene causes no problems in practical use, but fine wrinkles appeared in the film after steam sterilization.

In Example 7, in which the layer configuring a heat sealing surface is a mixture layer of a linear low-density polyethylene and a high-density polyethylene, inner surfaces of the pouch partially adhered tightly to each other after steam sterilization, and slight whitening was shown in the surface on which the adhesion portion was peeled. There was no tight adhesion between the inner surfaces of the pouch in Examples 4, 5, and 6.

INDUSTRIAL APPLICABILITY

According to the invention, it is possible to provide: an infusion bag film which uses a polyamide resin, which can be heat-sealed in a short period of time at a high temperature but has a problem in the hot water resistance in some cases, in a surface layer, and has reduced eluate in a pH test, that is, has excellent hot water resistance; and an infusion bag using the infusion bag film.

REFERENCE SIGNS LIST

10: INFUSION BAG FILM
11: SURFACE LAYER
12: ADHESIVE LAYER
13: HEAT SEALING LAYER
20A, 20B: INFUSION BAG

The invention claimed is:

1. An infusion bag film comprising:
a surface layer which is formed of a polyamide resin composition;
a heat sealing layer which is formed of a polyethylene resin composition containing a polyethylene as a main component; and
an adhesive layer which is provided between the surface layer and the heat sealing layer,
wherein the polyamide resin composition is obtained by blending 0.05 parts by mass to 1 part by mass of hydrotalcite with respect to 100 parts by mass of a polyamide resin formed of one or more of Nylon 11 and Nylon 12,
wherein the adhesive layer is a layer formed of an adhesive resin containing, as a main component, a copolymer of an olefin polymer composed of an ethylene, a propylene, or a combination thereof and an unsaturated monomer, and
wherein the infusion bag film is an unstretched film obtained by multi-layer T-die molding, or multi-layer coextrusion inflation molding.

2. The infusion bag according to claim 1, wherein the unsaturated monomer is an unsaturated carboxylic acid monomer or an anhydride monomer of an unsaturated dicarboxylic acid.

3. An infusion bag comprising:
a bag having walls;
the wall consisting of an infusion bag film comprising:
a surface layer which is formed of a polyamide resin composition;
a heat sealing layer which is formed of a polyethylene resin composition containing a polyethylene as a main component; and
an adhesive layer which is provided between the surface layer and the heat sealing layer,
wherein the polyamide resin composition is obtained by blending 0.05 parts by mass to 1 part by mass of hydrotalcite with respect to 100 parts by mass of a polyamide resin formed of one or more of Nylon 11 and Nylon 12,
wherein the adhesive layer is a layer formed of an adhesive resin containing, as a main component, a copolymer of an olefin polymer composed of an ethylene, a propylene, and
wherein the infusion bag film is an unstretched film obtained by multi-layer T-die molding, or multi-layer coextrusion inflation molding.

4. The infusion bag according to claim 3, wherein the infusion bag comprises multiple chambers for infusion.

5. The infusion bag according to claim 3, wherein the unsaturated monomer is an unsaturated carboxylic acid monomer or an anhydride monomer of an unsaturated dicarboxylic acid.

* * * * *